United States Patent [19]

Todd et al.

[11] Patent Number: 4,917,092

[45] Date of Patent: Apr. 17, 1990

[54] TRANSCUTANEOUS NERVE STIMULATOR FOR TREATMENT OF SYMPATHETIC NERVE DYSFUNCTION

[75] Inventors: Gregory A. Todd, Westerville; Michael H. Southworth; John P. Landino, both of Columbus, all of Ohio

[73] Assignee: Medical Designs, Inc., Westerville, Ohio

[21] Appl. No.: 218,722

[22] Filed: Jul. 13, 1988

[51] Int. Cl.$^4$ .............................................. A61N 1/36
[52] U.S. Cl. ................................................... 128/421
[58] Field of Search .................... 128/421, 422, 423 R

[56] References Cited

U.S. PATENT DOCUMENTS

| | | |
|---|---|---|
| 3,817,254 | 6/1974 | Maurer ................................. 128/421 |
| 4,210,151 | 7/1980 | Keller, Jr. ............................ 128/421 |
| 4,340,063 | 7/1982 | Maurer ................................. 128/421 |
| 4,759,368 | 7/1988 | Spanton et al. ...................... 128/421 |
| 4,763,656 | 8/1988 | Nauman ............................... 128/421 |

Primary Examiner—Lee S. Cohen

[57] ABSTRACT

A transcutaneous nerve stimulator and method for using the same are provided for use in treating sympathetic nerve dysfunction. The device includes an analog-to-digital and digital-to-analog converter, a nonvolatile random access memory, a preprogrammed microprocessor with masked memory and two output channels with respective jacks for electrodes. A dual line data bus interconnects the microprocessor, converter and RAM.

14 Claims, 2 Drawing Sheets

TRANSCUTANEOUS NERVE STIMULATOR FOR TREATMENT OF SYMPATHETIC NERVE DYSFUNCTION

BACKGROUND OF THE INVENTION

This invention relates to transcutaneous nerve stimulation and more particularly to a transcutaneous nerve stimulating device which represents an advancement in the treatment of sympathetic nerve dysfunction. This invention is directed to the providing of a transcutaneous nerve stimulator which is designed to be utilized in T.E.N.S. (Transcutaneous Electrical Nerve Stimulation) therapy. T.E.N.S. therapy is based on a non-invasive, non-narcotic concept of pain management which is non-addictive, is not subject to abuse, and does not interact with drugs. T.E.N.S. therapy has already proven to be an effective modality in treating the organic pain problems associated with the following conditions involving the central nervous system: chronic lumbar and cervical strains or sprains, degenerating disc disease, degenerative arthritic disease, neuropathies, neuralgias, post-lumbar laminectomy syndrome, post-thoracotomy syndrome, bursitis, postphlebitis syndrome, phantom limb syndrome, and tension and migraine headaches.

Early attempts to suppress organic pain and other neurophysical effects utilizing electrical stimulation occurred as early as 2,000 years ago when it was discovered that gout apparently could be successfully treated by placing the diseased extremities in a tub of water filled with electric eels. Later, headaches were treated using a similar approach. A detailed, scientific investigation was finally conducted by Professor Galvani of the University of Bologna, which investigation is credited with ultimately leading to the development in the 1800's of electrical equipment for suppression of organic pain associated with the central nervous system. The earliest therapeutic devices utilizing electrical stimulation for the most part featured a constant amplitude and rate. Examples of the early art are Benz, U.S. Pat. No. 646,793; Raymond et. al., U.S. Pat. No. 872,148; Tibbals, U.S. Pat. No. 1,059,090; and Call, U.S. Pat. No. 1,908,688. A major problem with electrical stimulation therapy has been accommodation, whereby the nerve being stimulated in effect accommodates itself over time to the electrical charge, such that the effectiveness of the treatment is diminished.

It took scientists a long time to discover and attempt to address the problem. Nemec, U.S. Pat. No. 2,622,601; DiPerma, U.S. Pat. No. 2,624,342; and Gratzl, U.S. Pat. No. 2,771,554 all disclose electrotherapeutic devices with at least one including means to vary the rate, amplitude or pulse width of the generated electrical pulse. However, merely being able to change either the rate, amplitude or pulse width still resulted at best in an individual having to manually adjust the controls prior to the occurrence of accommodation. The process was both labor intensive and inefficient, with respect to the quality of the therapy, since maximum pain relief for the central nervous system was not being provided.

In 1967, a Dr. Sweet at Massachusetts General Hospital developed the first T.E.N.S. unit. The effectiveness of T.E.N.S. therapy is believed to be based on its incorporating two major pain control theories. Under the so-called Gate Control theory, pain can be inhibited and suppressed by "closing the gate" on pain signals. This theory postulates that by providing electrical stimulation of a sufficiently high pulse amplitude, narrow pulse width and high pulse rate the electrical signals race up large myelinated fibers faster than the pain signals travel up smaller unmyelinated fibers. The neural impulses transmitting pain information to the brain thus become interrupted, and since the brain fails to receive the pain signals, no pain is perceived. The other theory incorporated in T.E.N.S. units is the Endorphin Theory, also known as the Endogenous Opiate Theory. This theory postulates that the sustained input of T.E.N.S. signals triggers the release of naturally occurring pain making endorphins and enkephalins (morphine-like substances). These natural substances block pain signals by a mechanism of binding to receptors in the brain where pain perception occurs and inhibit pain information from reaching the brain.

There is a known clinical correlation between amplitude and pulse width with regard to the efficacy of the stimulus. As one shortens the duration of a pulse, its amplitude must be increased to maintain the efficacy of the stimulus. This relationship when plotted graphically is known as a strength-duration curve. Thus not only must the ideal T.E.N.S. units have adjustable amplitude and pulse width, but it must also be able to modulate those values in such a way as to approximate the strength-duration curve in the maximum sensory threshold.

This explains the shortcomings in Reiner, U.S. Pat. No. 2,808,826 which disclosed a unit which permitted instantaneous changes in pulse width and amplitude to two pre-set points along the strength-duration curve, and Maurer, U.S. Pat. No. 4,340,063 which disclosed a unit having its amplitude modulate in response to modulations in pulse width so as to approximate a portion of the strength-duration curve. The rate in Maurer was manually adjustable, but only to the extent taught by Miller, U.S. Pat. No. 4,084,595.

The problem with accommodation in the treatment of pain associated with the central nervous system was addressed in Spanton et al, U.S. Ser. No. 936,828, now U.S. Pat. No. 4,759,368. That particular device constituted an advancement in treatment of organic pain associated solely with the central nervous system. However, studies have shown that between 80 and 90% of chronic and acute pain involves sympathetic nerve dysfunction, and that in fact sympathetic nerve dysfunction constitutes between 10 and 80% of the actual problem. Sympathetic nerve dysfunction involves treating of the autonomic nervous system.

The sympathetic nervous system is part of the automatic network primarily responsible for vasoconstriction of arterial beds (i.e., the increase or decrease of blood flow in specific areas). This network controls arterial blood pressure, gastrointestinal mobility secretions, urinary output, sweating, body temperature regulation and artery blood flow. This system is comprised of pre- and post-ganglionic fibers and is involved either directly or indirectly in most chronic pain patients. In cases of sympathetic nerve dysfunction such as causalgia or non-specific lumbar or thoracic sympathetic dysfunction, these fibers are the primary causative agent. With many chronic pain patients, the sympathetic nervous system establishes an inhibitory reflex of vasoconstriction in the injured area resulting in hypoxemia. This lack of oxygen prevents adequate healing and in fact increases the pain in that area. It has only been within the past ten years that physicians have found that some relief for sympathetic nerve dysfunction can be obtained through T.E.N.S. treatment with a low frequency of pulsation, since sympathetic nerves have a repolarization time of 0.3 to 1.3 milliseconds.

Although physicians believe T.E.N.S. may be helpful in treating sympathetic nerve dysfunction, an unsolved problem relates to the amount of actual treatment time available using existing T.E.N.S. units. For example, it has not been uncommon to treat an individual for sympathetic nerve dysfunction for a period of five to ten minutes using low frequency burst pulsation with a therapist or doctor present. However, at the end of that time period, the amount of pain associated with the central nervous system and the patient's nociceptors is such that the patient must undergo treatment for perhaps the next four hours using high frequency pulsation to address central nervous system pain. Thus, after an extended period of time of T.E.N.S. treatment, the patient has only had a few minutes which actually addressed sympathetic nerve dysfunction with treatment of the sympathetic nerves occurring for less than 5% of the T.E.N.S. treatment time. One could not address problems of the autonomic and central nervous systems simultaneously.

Patients who tried to constantly, manually switch modes in an attempt to overcome the problem usually sacrificed maximum pain relief to either the autonomic or central nervous system. Plus the constant switching had to be prolonged for several hours for the treatment to even be nominally effective. Thus, prior devices and medical techniques have been extremely inefficient, despite the severity of the problem and the longfelt need.

Furthermore, the slow response time of the sympathetic nervous system precludes CNS strength-duration modulation with its high rates and relatively narrow widths. Thus treatment of sympathetic nerve dysfunction with traditional CNS strength-duration modulation does not result in the patient obtaining adequate pain relief.

Therefore, due to the problems associated with the treatment of sympathetic nerve dysfunction by T.E.N.S. therapy, the traditional medical approach has been to treat the sympathetic nervous system with various medications, including sympatholectyic drugs and various sympathomimetric drugs. These types of drugs have significant side effects either directly on the central nervous system or on generalized sympathetic functions, such as increased blood pressure or tachycardia. Thus, current approaches to treatment of sympathetic nerve dysfunction are either inefficient or entail significant physiological and pharmacologic side reactions. Therefore it is apparent that the need exists for an improved T.E.N.S. unit and methodology of treatment.

SUMMARY OF THE INVENTION

In accordance with this invention, a transcutaneous nerve stimulator is provided for advantageous use in T.E.N.S. therapy directed to sympathetic nerve dysfunction along with the method for using the unit. In accordance with this invention, the amplitude, pulse width and rate are all modulated with respect to one another so that both the autonomic and central nervous systems are simultaneously stimulated for significantly more than the amount of time associated with prior T.E.N.S. units.

Included in the stimulator are a plurality of circuits, designed such that the unit may operate in any one of five modes: burst, conventional single amplitude/single pulse width, pulse width modulated, CNS strength-duration/rate modulated, and sympathetic strength-duration/rate modulated. In this final mode, for the first time, sympathetic nerve dysfunction can be both effectively and efficiently treated using T.E.N.S. therapy.

Pulses of varying pulse width and amplitude are generated by the device, with at least one of the controls for amplitude, pulse width and rate being independently adjustable for the first three modes and with all three control means having their respective values modulated when in the fourth and fifth modes. In the fourth and fifth modes, the amplitude control means and pulse width control means are electrically coupled, with the rate control means interacting with the product of the coupling, so as to provide maximum sensory stimuli and maximum pain relief.

The primary objective of this invention is to provide a nerve stimulation device and method for use in T.E.N.S. therapy that addresses the problem of sympathetic nerve dysfunction. An important aspect of this invention is the maximization of stimulation of the autonomic nervous system.

Another objective is the providing of a T.E.N.S. unit which can provide a plurality of operating modes, including one for treatment of sympathetic nerve dysfunction. This important objective is furthered by the providing of several circuits in selectively adjustable mode control means which permits any one of five operating modes to be chosen.

Still another objective is the providing of a T.E.N.S. unit which permits the simultaneous stimulation of the autonomic and central nervous systems. This objective is furthered by allowing this stimulation to be both antidromic and orthodromic.

Yet another objective is to provide a T.E.N.S. unit, having all the capabilities of this invention, that is of extremely economical construction and is particularly easy to operate. This objective is furthered by supplying a T.E.N.S. unit having all the characteristics of this invention as a portable, hand-held unit.

These and other objects and advantages of this invention will be apparent from the following description, the accompanying drawings and the appended claims.

DETAILED DESCRIPTION OF THE INVENTION

Figure 1:
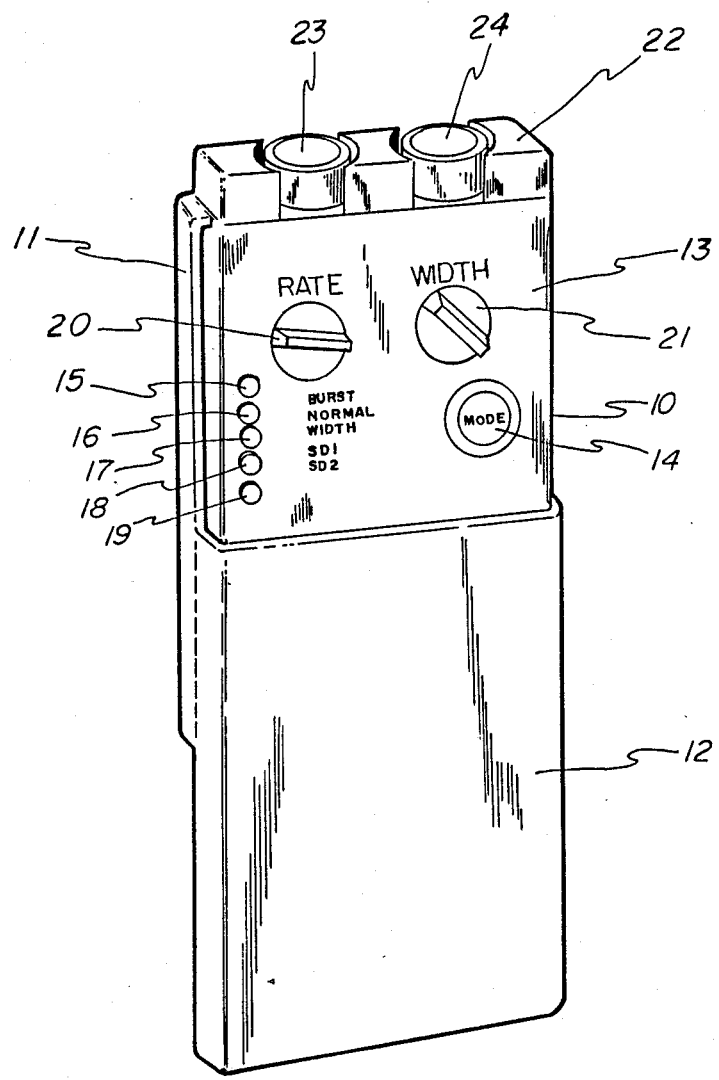
FIG. 1 is a perspective view of a transcutaneous nerve stimulator in its operative condition, showing the various controls.

Having reference to the drawings, attention is directed first to FIG. 1 which illustrates a transcutaneous nerve stimulator embodying this invention and designated generally by the numeral 10. This T.E.N.S. unit 10 has a base 11 and cover 12 which are slidably interconnected, such that when the unit is in use, the cover 12 is slidably displaced to reveal front display panel 13. The front display panel 13 features several adjustable control means. Mode selector 14 permits the unit 10 to operate in five distinct modes. Indicator lights 15, 16, 17, 18, and 19 correspond to burst, normal, or conventional single amplitude/single pulse width, width modulated, strength-duration/rate modulated and sympathetic strength-duration/rate modulated modes, with a specific light being activated in response to the mode selected. The indicator lights permit the user to know what mode the unit 10 is in for reasons of safety. Also on the front display panel 13 are rate and pulse width control means 20 and 21 respectively.

The unit 10 also features a top display panel 22 featuring two amplitude control means 23 and 24, each of which are associated with electrodes which are attached to the skin of the patient. Electrode outlets (not shown) are located on the base 11 adjacent to the rear of top display panel 22. Also located there is a low battery light (not shown) which serves to apprise the user of the charge conditions of the energy source used to power the transcutaneous nerve stimulator of this invention.

Figure 2:
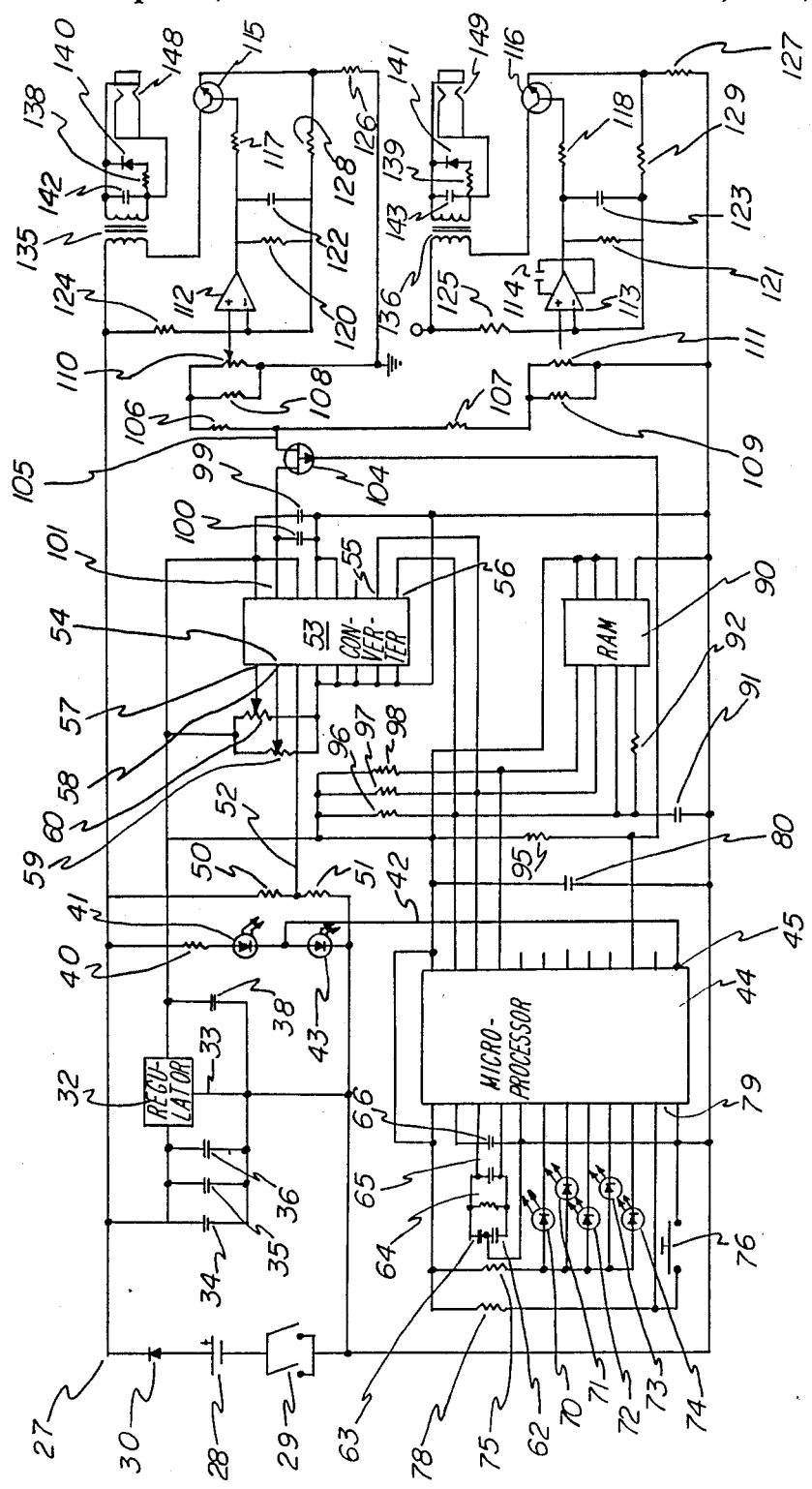
FIG. 2 is a schematic diagram of the circuitry used in the preferred embodiment.

Now that the general physical features of the apparatus 10 have been described, consideration will now be given to the electrical circuitry used in implementing the preferred embodiment. Referring to FIG. 2, the circuit 27 obtains its power by battery 28 with the circuit 27 being activated by switch 29. The presence of diode 30 protects against reversal. A regulator 32 is used to take the 9 volt supply and provide a regulated 5 volt supply. A shown, the regulator 32 has a center connection to ground and three capacitors 34, 35, and 36 to filter the 9 volt supply. Preferably, these filter capacitors are 330 mf, 22 mf, and 3.3 mf capacitors. The output from regulator 32 supplies 5 volts to the unit 10 with the filter for the 5 volt supply being a 22 mf capacitor 38.

A 10K resistor 40 limits the current which passes through LED 41, with this LED emitting a red light and serving as the on/off indicator light. A center tap 42 between LED 41 and LED 43, which is a yellow light emitting diode, connects to microprocessor 44 at pin 45, which acts as a current sink under normal power supply conditions and as a current source under insufficient voltage power supply conditions. The microprocessor has a masked memory.

47K resistor 50 and 56K resistor 51 form a voltage divider to sense the battery potential and set the "low-battery" detection levels. Center tap 52 goes to converter 53. This converter is an analog-to-digital and digital-to-analog converter having a dual line data bus. The center tap is connected to the converter at pin 54. Hence, the signal at pin 54 is converted and sent out at pins 55 and 56 to microprocessor 44. When the battery level drops to 7 volts, the yellow light 43 will flash by toggling pin 45 of the microprocessor. When pin 45 goes high, the yellow light will be turned on. When resistors 50 and 51 sense a battery level of only 6 volts, then the yellow light will stay on constantly and no pulses will be sent to the output circuit of the T.E.N.S. unit.

The converter 53 also has pins 57 and 58 connected to 100K potentiometers 59 and 60 which are associated with the pulse width and rate respectively. Pins 54, 57, and 58 but all have their input independently converted to digital data and independently sent over the data bus at pins 55 and 56. The microprocessor 44 receives the data, then calculates the width and frequency of pulses to be generated from pin 61 of microprocessor 44.

Microprocessor 44 utilizes a standard time base generator which includes a 47 pf capacitor 62, a 47 pf capacitor 63, a 1M resistor 64, and a crystal 65. A 1 mf capacitor 66 resets microprocessor 44 when use of the unit is resumed after a period of inactivity. The invention also includes a plurality of LEDs 70, 71, 72, 73, and 74 which correspond to the burst, normal, width, strength-duration/rate and sympathetic strength-duration/rate modes. A 2.2K limiting resistor 75 limits the current in the LEDs 70-74. A mode select switch 76, having the physical embodiment as shown at 14 in FIG. 1, is also provided. The 22K resistor 95 serves as a pull-up resistor for the open collector output pin 61 of microprocessor 44. The unit also makes use of one of four 56K resistors, comprising the resistor SIP, as a pull-up resistor which holds pin 79 at 5 volts when the unit is operating in a particular mode of stimulation, and also as a current limiter preventing excessive power loss to ground when mode selector switch 76 is depressed. A 1 mf capacitor 80 is dedicated for noise filtering at microprocessor 44.

Microprocessor 44 also sends digital information to a non-volatile RAM 90, which stores the mode of operation and maintains it during periods of inactivity. The hardware associated with the memory unit of this invention is very basic in that it includes a 47 pf capacitor 91 and a 2.2K resistor 92. The three 56K pull-up resistors 96, 97, and 98, along with resistor 78 comprise the resistor SIP. Resistors 96 and 97 are used as pull-up resistors for the dual line data bus and resistor 98 serves as a pull-up resistor for the enable line of the non-volatile RAM device 90. 22 mf capacitor 99 serves as a filter for the power connection of the converter, while 3.3 mf capacitor 100 serves as the analog signal output capacitor.

Pin 61 of microprocessor 44 is the source of the generated pulses to be amplified and conveyed to the patient via electrodes. Pin 61 is connected to the gate of P-channel FET 104 which controls the passage of current from pin 101 of the converter 53 to the two individual signal amplifier stages. The signal from pin 61 of microprocessor 44 contains the pulse rate and pulse width information and controls the gate of FET 104. The microprocessor 44 sends the amplitude modulation information (via the data bus) to the converter 53, which results in cyclic variance of the FET 104 source voltage via the converter 53 analog output at pin 101. The resultant signal at the FET's 104 drain 105 contains all modulated and unmodulated parameter information with the exception of the user amplitude controls.

There are two identical output amplification circuits which provide individual channels of stimulation. 56K resisters 106 and 107 provide the necessary signal isolation. 10K trimming potentiometers 108 and 109 limit the maximum level of amplitude available to the user via 10K control potentiometers 110 and 111. The wipers of control potentiometers 110 and 111 serve as the inputs to signal amplifiers 112 and 113. Capacitor 114 serves as a filter for both operational amplifiers since they are housed in the same physical package. The amplifier outputs drive NPN switching transistors 115 and 116 through 390K limiting resistors 117 and 118.

120K resistors 120 and 121 and 150pf capacitors 122 and 123 are standard output feedback network components. Resistors 124 and 125 are 10M pull-up resistors for the signal amplifiers' inverting inputs. 27K resistors 126 and 127 and 1K resistors 128 and 129 are emitter stabilization resistors. Transistors 115 and 116 serve as drivers for the primary coils of transformers 135 and 136. The induced current through the secondary coils creates the signal potential between the output electrodes. 10K resistors 138 and 139, diodes 140 and 141 and 0.0047mf capacitors 142 and 143 provide loading stabilization.

In actual operation, once the unit is turned on, data is read in microprocessor 44 from RAM 90 indicating the mode the unit was in when last in use, as well as from potentiometers 59 and 60. Then the mode is selected. Assuming that the advantageous treatment mode of this invention is selected, the microprocessor has been preprogrammed such that it can determine the specific adjustments that need to be made to pulse width and frequency at any specific point in time, so that width and amplitude closely approximate the strength-duration curve in the maximum sensory threshhold. For example, if the rate is set at 100, then that value is converted from analog-to-digital and travels through the dual line data bus to microprocessor 44 at which time the microprocessor's program generates pulses in 12 second cycles such that after half the cycle the pulse rate has been reduced by 90%. Meanwhile, pin 101 of converter 53 receives by the bus the voltage values associated with those pulses then outputs them as the source to field effect transistor 104. The signal out of pin 61 of the microprocessor therefore determines the frequency and width of the pulses while pin 101 of converter 53 determines how much amplitude will pass through resistors 106 and 107.

It has been discovered that through the utilization of specific parameters involving pulse width, pulse rate, and amplitude, that a T.E.N.S. unit can be used effectively and efficiently in the treatment of sympathetic nerve dysfunction. Specific indications where this invention is believed to prove effective, whereas no prior T.E.N.S. unit has, include reflexive sympathetic dystrophy, post-herpatic neuralgia and trigenital neuralgia.

The values associated with this discovery are disclosed in the following Table.

| Point in Cycle | 0 Seconds | 6 Seconds | 12 Seconds |
| --- | --- | --- | --- |
| Pulse Amplitude | 100% | 87% | 100% |
| Pulse Width | 100% | 160% | 100% |
| Pulse Rate | 100% | 10% | 100% |

As can be seen from the above, when amplitude decreases by 13%, pulse width increases by 60% and pulse rate decreases by 90% from the original or maximum settings. Significant relief can thus be obtained for individuals suffering from sympathetic nerve dysfunction who heretofore had been poor candidates for T.E.N.S. therapy.

In actual therapy, a physician may prescribe that initial treatment in the SD2 mode last for two days at twenty-two hours per day, followed by twelve to fourteen hours of treatment per day until relief is obtained. These periods of treatment need not be in the presence of medical personnel.

Utilization of this T.E.N.S. unit permits the suppression of pain associated with sympathetic nerve dysfunction by the simultaneous stimulation of the autonomic and central nervous systems. Sympathetic nerve dysfunction is addressed by the low frequency of pulses at the mid-point of the cycle, while the central nervous system pain associated with a person's nociceptors is addressed at the higher pulse rates and consequently lower pulse widths. As opposed to the prior art, wherein treatment of the autonomic nervous system occurred for less than 5% of the time treatment occurred to the central nervous systems, this invention permits the autonomic nervous system to be stimulated for a greater amount of time relative to the central nervous system. The amount of time may be more than 8%, and possibly more than 10% of the treatment time.

So as to approximate the strength-duration curve associated with the treatment of pain related to the central nervous system, the pulse widths of the generated pulses increase when the amplitude decreases and the pulse width decreases when the amplitude increases, with the pulse rate being at its minimum when the pulse width is at its maximum. Additionally, the treatment afforded by the preferred embodiment of this invention permits the stimulation to be both antidromic and orthodromic.

It will be readily apparent from the foregoing detailed description of the preferred embodiment of this invention, that a particularly novel and extremely effective T.E.N.S. device is provided. The device is relatively simple to fabricate and results in a device which provides a degree of pain relief heretofore unknown in the treatment of pain associated with the sympathetic nervous system as far as the efficiency and effectiveness of treatment.

While the form of apparatus and method herein described constitutes a preferred embodiment of this invention, it is to be understood that the invention is not limited to this precise form of apparatus, and that changes may be made therein without departing from the scope of the invention which is defined in the appended claims.

What is claimed is:

1. A method for using one T.E.N.S. unit for efficient suppression of pain associated with sympathetic nerve dysfunction which comprises the steps of
   generating pulses,
   modulating the pulse width and amplitude of the generated pulses over a modulation cycle to vary in a prescribed manner so as to stimulate within each modulation cycle the autonomic and central nervous systems of said person, such that said sympathetic nerve dysfunction is treated with a low frequency of pulses while through the utilization of strength-duration modulation at higher pulse rates, said person's nociceptors are addressed, such that said autonomic nervous system is stimulated for more than 5% of the amount of time as said central nervous system, and
   conveying said pulses to a person experiencing pain associated with sympathetic nerve dysfunction.

2. The method according to claim 1, wherein said modulation cycle features generated pulses of varying values of pulse widths and amplitudes, said values of pulse widths increasing when said values of amplitude decrease and said pulse width values decreasing when said amplitude values increase, said generated pulses having a value for its pulse rate at its minimum when said value for pulse width is at its maximum.

3. The method according to claim 2, wherein said stimulation is antidromic and orthodromic.

4. The method according to claim 2, wherein said generated pulses are of specific amplitude and pulse width values which if plotted would approximate the strength-duration curve in the maximum sensory threshhold.

5. The method according to claim 2, wherein said modulation cycle occurs in cycles of twelve seconds.

6. The method according to claim 5, wherein said pulse rate decreases to 10% of its value at the maximum of said cycle.

7. A transcutaneous nerve stimulating device for efficient treatment of sympathetic nerve dysfunction comprising means for generating a plurality of pulses, amplitude, pulse width and rate modulation control means, which cause the amplitude, pulse width and rate of the generated pulses to vary in a prescribed manner which permits the stimulation of the autonomic and central nervous systems by generated pulses, said amplitude control means interacting with said pulse width control means so as to maintain a mode featuring strength-duration modulation such that the values associated with pulse width and amplitude vary inversely and with the pulse rate being at its minimum when said pulse width is at its maximum, and means for conveying said pulses to a person experiencing pain associated with sympathetic nerve dysfunction.

8. A device according to claim 7, wherein said generated pulses are of specific amplitude and pulse width values which if plotted would approximate the strength-duration curve in the maximum sensory threshhold.

9. A device according to claim 7, wherein said strength-duration modulation occurs in cycles of twelve seconds.

10. A device according to claim 7, wherein said mode includes rate modulation from a maximum value, said pulse rate decreasing to 10% of its maximum value.

11. A method for using one T.E.N.S. unit for efficient suppression of pain associated with sympathetic nerve dysfunction which comprises the steps of generating pulses, modulating the pulse width and amplitude of the generated pulses over a modulation cycle to vary in a prescribed manner so as to stimulate within each modulation cycle the autonomic and central nervous systems of said person, the stimulation being such that said sympathetic nerve dysfunction is treated with a low frequency of pulses while addressing, without manual resetting of treatment modes, a person's nociceptors through the utilization of strength-duration modulation at higher pulse rates, and conveying said pulses to a person experiencing pain associated with sympathetic nerve dysfunction.

12. The method of claim 11 wherein stimulating said autonomic and central nervous systems occurs during the same treatment time.

13. The method of claim 12 wherein stimulating said autonomic and central nervous systems occurs during the same mode.

14. The method of claim 11 wherein said stimulation of both the autonomic and the central nervous systems occurs while said one T.E.N.S. unit is modulating.

* * * * *